United States Patent [19]
Yamamoto et al.

[11] Patent Number: 4,839,167
[45] Date of Patent: Jun. 13, 1989

[54] EMULSION TYPE HAIR COSMETIC

[75] Inventors: Hiromi Yamamoto, Sakura; Hideko Ishido, Tokyo, both of Japan

[73] Assignee: Kao Corporation, Tokyo, Japan

[21] Appl. No.: 90,343

[22] Filed: Aug. 28, 1987

[30] Foreign Application Priority Data

Sep. 18, 1986 [JP] Japan ................... 61-220045

[51] Int. Cl.$^4$ ............................... A61K 7/11
[52] U.S. Cl. ......................... 424/71; 424/47; 424/DIG. 2; 514/941
[58] Field of Search ............... 424/47, 70, 71, DIG. 1, 424/DIG. 2; 514/63, 941

[56] References Cited

U.S. PATENT DOCUMENTS 4,311,695  1/1982  Starch ............................ 514/63
4,675,179  6/1987  Suzuki et al. ................... 514/941

FOREIGN PATENT DOCUMENTS 0116207  6/1983  European Pat. Off. .
0154837  2/1985  European Pat. Off. .
0155806  11/1985  European Pat. Off. .

Primary Examiner—Ellis P. Robinson
Assistant Examiner—Susan S. Rucker
Attorney, Agent, or Firm—Oblon, Spivak, McClelland, Maier, & Neustadt

[57] ABSTRACT

An emulsion type hair cosmetic comprising: (a) 0.1 to 5% by weight of a dimethylpolysiloxane polyoxyalkylene copolymer having a cloud point of 20° to 45° C., (b) 0.02 to 2.5% by weight of non-ionic surface active agent having an HLB value of not less than 10, (c) 0.01 to 0.5% by weight of ionic surface active agent, (d) 0.05 to 10% by weight of silicone oil, (e) 0.1 to 10% by weight of a polymer for fixing hair, which is soluble in water or an ethanol/water mixture of 50/50 weight ratio, (f) 2 to 40% by weight of ethanol, and (g) 30 to 97% by weight of water. The hair cosmetic possesses an excellent hair dressing or setting ability, a low stimulus to the skin and a good storage stability. It can preserve the fragrance very stably and afford a good feeling on use.

1 Claim, No Drawings

EMULSION TYPE HAIR COSMETIC

BACKGROUND OF THE INVENTION

1. Field of the Invention

This invention relates to an emulsion type hair cosmetic and more particularly, to an emulsion type hair cosmetic capable of providing a good feeling to the hair which is dressed or set using the same.

2. Description of the Background

A cold perm treatment is widely practiced in order to have hair waved or curled. Set lotions, hair sprays and foam hair dressings are employed in order to fix the hair style and to beautifully dress up the hair thus treated by cold perming. They are also used, even when hair is not cold permed, in order to give a temporary wave or curl and to prevent the hair from getting disheveled.

In formulating such set lotions, hair sprays and foam hair dressings, polymeric compounds for hair fixing are used mixed with a suitable solvent such as water, a lower alcohol, a mixture of water and a lower alcohol and the like. The mixture is used as it is in the case of set lotions, and is made into an aerosol mixed with a suitable liquified gas as a propellant in the cases of hair sprays and foam hair dressings.

Polymeric compounds conventionally used for fixing hair, however, have a surface tension which is higher than the critical surface tension of the hair, so that polymers tend to form a small lump and deposit on the hair as island-like spots. Thus, they can not form a uniform coat on hair. This leads to an insufficient hair-curl or wave retention, especially at a high humidity, and an impaired feeling to touch. Moreover, deposited spots of the polymeric compound may flake off when the hair is combed, thus making the hair less glossy and smooth.

In order to eliminate these drawbacks in the conventional hair-care products, studies have been made to formulate additives such as cosmetic oils and fats, or surface active agents, but there has been so far found no additive which is sufficiently effective. The use of a material with a surface tension which is smaller than the critical surface tension of the hair will help the cosmetic form a uniform coat on the hair. This, however, necessitates use of an oil which is less sticky and which has a smaller surface tension. It is known that the addition of silicone oil to a composition will decrease its surface tension to a value smaller than the critical surface tension of the hair and help the composition forming a uniform coat on hair. Silicone oil, however, has disadvantages of a poor dissolving ability with polymers, ordinarily used surface active agents and other oil components, and of being extremely difficult to be emulsified. It is thus difficult to obtain a uniform and stable mixture using silicone oil.

SUMMARY OF THE INVENTION

The inventors have carried out extensive studies for the purpose of preparing a hair cosmetic which is capable of forming a uniform coat on hair, possessing a good hair-wave or curl retention ability, and yet giving a good feeling to touch. As a result, it was found that a fine, homogeneous and stable emulsion with a low viscosity and containing as major components silicon oil and a polymeric compound could be obtained, using, as an emulsifier, a mixture of a specific dimethylpolysiloxane polyoxyalkylene copolymer, nonionic surface active agent with an HLB value of not less than 10 and an ionic surface active agent, adding to the mixture under agitation a water phase with an ethanol concentration of a specified range, thus forming a gel-like or high viscous single phase in the course of the manufacturing process. The inventors have further found that a hair cosmetic which satisfies the above requirements could be obtained by using this emulsion. Such findings have led to the completion of this invention.

Accordingly, an object of this invention is to provide an emulsion type hair cosmetic comprising:

(A) 0.1 to 5% by weight of a dimethylpolysiloxane polyoxyalkylene copolymer having a cloud point of 20° to 45° C., (B) 0.02 to 2.5% by weight of non-ionic surface active agent having an HLB value of not less than 10, (C) 0.01 to 0.5% by weight of ionic surface active agent, (D) 0.05 to 10% by weight of silicone oil, (E) 0.1 to 10% by weight of a polymer for fixing hair which is soluble in water or an ethanol/water mixture of 50/50 weight ratio, (F) 2 to 40% by weight of ethanol, and (G) 30 to 97% by weight of water.

DETAILED DESCRIPTION OF THE INVENTION AND PREFERRED EMBODIMENTS

The dimethylpolysiloxane polyoxyalkylene copolymer, the component (A), used in the present invention is typified by the compound represented by the following formula (I):

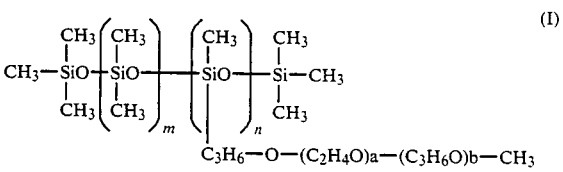

in which a represents a value of from 10 to 25, b represents a value of from 25 to 35, m represents a value of from 60 to 80 and n represents a value of from 3 to 8. It is desirable that these silicon oils have a viscosity of from 0.5 to 1,000 centistokes.

Such compounds can be commercially available in a trade name, Silicon L-7001 (product of Nippon Uniker), for instance.

The surface active agent, the component (B), may be those having an HLB value of not less than 10, which may be used singly or in combination with two or more others. In particular, surface active agents having an HLB value of from 11 to 16 are preferred. Specific examples of such surface active agents include polyoxyethylene alkyl ethers, polyoxyethylene fatty acid esters, polyoxyethylene sorbitan fatty acid esters, polyoxyethylene glycerine fatty acid esters, polyoxyethylene hydrogenated castor oils, polyglycerine fatty acid esters, sucrose fatty acid esters, and the like.

The ionic surface active agent which is the component (C) may be an anionic, cationic or amphoteric surface active agent. Among them a preferred is a cationic surface active agent, particularly a quaternary ammonium salt compound represented by the following formula (II):

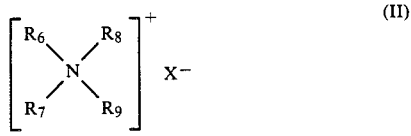

in which one or two of $R_6$, $R_7$, $R_8$ and $R_9$ represent linear or branched alkyl or hydroxyalkyl groups having from 8 to 22 carbon atoms, and the others represent alkyl or hydroxyalkyl groups each having from 1 to 3 carbon atoms, benzyl groups or polyoxyalkylene groups containing not mere than 10 oxyalkylenes, and X represents a halogen atom or alkyl sulfate group.

The component (D), a silicon oil, is exemplified by polysiloxanes represented by the following formulae (III) to (V), or a mixture thereof.

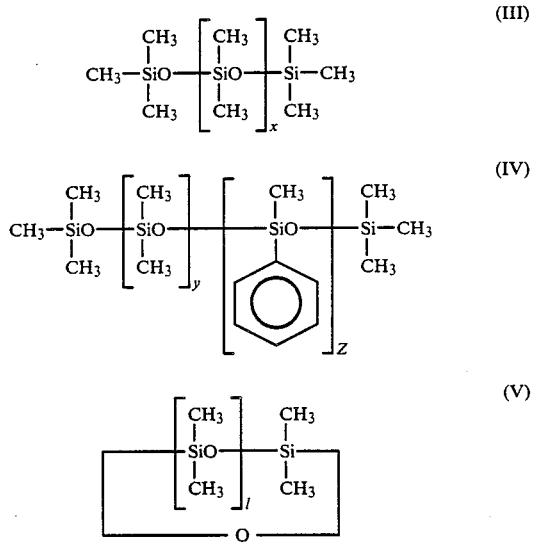

in which x is a value of from 4 to 100, z is a value of not less than 1, y+z is a value of from 1 to 100 and l is a value of from 2 to 5.

The component (E), which is a polymer soluble in water or an ethanol/water (50/50 by weight) mixture, may be those conventionally employed for set lotions and hair sprays. Following compounds are given as examples of such monomers:

(1) Polyvinylpyrrolidone compounds, such as polyvinylpyrrolidone and a copolymer of vinylpyrrolidone and vinyl acetate.

(2) Acidic polyvinylether polymeric compounds, such as a low alkyl half ester of copolymer of methylvinylether and maleic anhydride.

(3) Acidic polyvinyl acetate polymeric compounds, such as copolymer of vinyl acetate and crotonic acid.

(4) Acidic acrylic polymeric compounds, such as acrylic acid alkyl ester-methacrylic acid alkyl ester copolymer prepared by copolymerizing a small amount of acrylic acid or methacrylic acid.

(5) Dimethylhydantoine formaldehyde resins.

When the above polymeric compound has an acid group, it is desirable to use it after neutralizing all or portion of such acid group. Although there is no specific limitation to the alkali used for neutralizing such acid group, preferred are 2-amino-2-methyl-propanol, 2-amino-2-methyl-1,3-propanediol, triisopropanol amine and the like.

Several of other optional ingredients, desirably cosmetic oils, may be added other than the above-mentioned components which are the essential components of the emulsion type hair cosmetic of this invention. A wide variety of cosmetic oils which are conventionally used for cosmetics may be used in the present invention. These may include glycerides such as castor oil, olive oil, coconut oil and mink oil; waxes such as beeswax, spermaceti, lanolin and carnauba wax; hydrocarbons such as liquid paraffin, seresin and squalane; alcohols such as cetyl alcohol, oleyl alcohol and hexadecyl alcohol; and esters such as isopropyl myristate and oleyl oleate. Among them particularly preferred are oils and fats obtained from plants or animals, or synthetic esters, which are liquid or paste at normal temperature and which have an ester bond in a molecule, such as castor oil, olive oil, avocado oil, mink oil, lanolin, liquid lanolin, decyl oleate, lanolin acid isopropyl and the like. Liquid paraffin is also a preferred cosmetic oil component. The amount of these cosmetic oils to be added may be preferably 0.01 to 3.0% by weight of the total amount of the composition. The emulsion type cosmetic of this invention may be sealed in a container together with a propellant like a liquified petroleum gas to serve it in a form of spray or mousse. A perfume or coloring agent may be formulated to add to a commercial value of the product. An antiseptic or antioxidant may be added for the purpose of preventing changes in properties of the composition upon lapse of time.

In preparing the emulsion type composition of this invention, a single phase, gel-like viscous product is first prepared by adding to a mixture of the components (A) through (D) from 0.5 to 5 parts by weight, based on said mixture, of an ethanol/water mixture containing the component (E), weight ratio of ethanol/water being 20/80 to 70/30, preferably 30/70 to 60/40. The viscous product thus obtained is further added with ethanol to afford an oil-in-water emulsion. Water or an ethanol/water mixture may be further added to the thus-obtained emulsion, as required, to make the weight ratio of water/ethanol of the product to from 50/50 to 2/98. It is desirable to control the temperature of water or the ethanol/water mixture to be added at the last stage of the process in a range of from 5° to 45° C.

It is imperative that the proportions of each of the components (A) through (G) be in the range as prescribed above. Otherwise, the system can not form a stable emulsion, and thus the composition can not provide a uniform coat on hair and will provide only insufficient curl retaining ability and poor feeling to touch.

Favorable characteristics of the emulsion type hair cosmetic composition of this invention is considered to be afforded by the properties of silicone oil. In spite of the fact that the silicon oil is sparingly soluble in polymers, common surface active agents and other oil components, and thus it is very difficult to obtain a homogeneous and stable mixture containing silicon oil, it is possible according to the present invention to emulsify silicon oil into a very stable system.

The emulsion type hair cosmetic of this invention possesses an excellent hair dressing or setting ability, a low stimulus to the skin and a good storage stability. It can preserve the fragrance very stably and afford a good feeling on use. Thus, the composition is an excellent hair cosmetic.

Other features of the invention will become apparent in the course of the following description of the exemplary embodiments which are given for illustration of the invention and are not intended to be limiting thereof.

EXAMPLES

EXAMPLE 1

Bundles of hair 18 cm long and weighing 1.5 g were wetted by water, wound round a rod, and left over to get dried. The dried and curled bundles of the hair were taken out of the rod, and hair sprays having formulations as described in Table 1 were applied to each of the bundles by spraying the content for 5 minutes. The bundles were then left over to dry.

The curled-up bundle were suspended in a box which was maintained at a temperature of 30° C. and a relative humidity of 90%, to observe the elongation of the curled hair at this highly humid conditions. The curl retention was determined taking the length of the bundle immediately after it was suspended in the box as 100% and the original length of the hair, i.e. 18 cm as 0%.

Formulations of the tested hair sprays, the curl retention property and other properties of each of the sprays are shown in Tables 1, 2 and 3, respectively.

TABLE 2

| | Curl Retention at 30° C. and relative humidity of 90% | | | | |
|---|---|---|---|---|---|
| | Time left over | | | | |
| | 5 min. | 10 min. | 30 min | 1 hour | 2 hours |
| Inventive Composition | | | | | |
| A | 92.0% | 80.0% | 75.3% | 73.8% | 66.2% |
| B | 93.0 | 85.5 | 79.5 | 73.2 | 65.0 |
| C | 95.5 | 87.2 | 80.6 | 75.7 | 66.6 |
| D | 94.1 | 87.0 | 80.2 | 75.0 | 66.4 |
| Comparative Composition | | | | | |
| E | 85.2 | 75.9 | 56.2 | 40.8 | 20.5 |
| F | 30.2 | 20.8 | 15.2 | 8.5 | 6.9 |
| G | 52.5 | 45.3 | 38.7 | 20.5 | 18.8 |
| H | 55.1 | 48.2 | 40.1 | 35.2 | 30.3 |

TABLE 3

| | Items Evaluated | | | | |
|---|---|---|---|---|---|
| | Conditions of the coat | Ability to keep the dressed hair | Tendency of flaking | Stickiness | Feeling to touch |
| Inventive Composition | | | | | |
| A | uniform | good | non | non | good |
| B | uniform | good | non | non | pretty well |
| C | uniform | good | non | non | good |
| D | uniform | good | non | non | good |
| Comparative Composition | | | | | |
| E | not uniform | bad | tend to flake | sticky | bad |
| F | uniform | bad | non | non | good |
| G | not uniform | bad | tend to flake | sticky | bad |
| H | not uniform | bad | tend to flake | sticky | bad |

The emulsion type hair cosmetic compositions prepared by the above example exhibited an excellent curl retention ability, less flaking tendency and good feeling to touch.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

TABLE 1

| | (Formulation wt %) | | | | | | | |
|---|---|---|---|---|---|---|---|---|
| | Inventive Composition | | | | Comparative Composition | | | |
| Components | A | B | C | D | E | F | G | H |
| Vinyl acetate/crotonic acid copolymer (1) | 2.0 | 2.0 | 2.0 | 2.0 | 2.0 | — | 2.0 | 2.0 |
| 2-amino-2-methyl-1,3-propane diol | 0.2 | 0.2 | 0.2 | 0.2 | 0.2 | — | 0.2 | 0.2 |
| Dimethyl polysiloxane polyoxyalkylene copolymer (Cloud point 30° C.) (2) | 0.5 | 0.5 | 0.93 | 0.5 | 0.5 | 0.5 | 0.05 | 0.9 |
| POE(20) Sorbitan monooleate (HLB 15) | 0.5 | 0.4 | 0.12 | 0.5 | — | 0.5 | 0.65 | 0.31 |
| Sorbitan monooleate (HLB 4.3) | — | — | — | — | 0.5 | — | — | — |
| Stearyl trimethylammonium chloride | 0.1 | 0.08 | 0.05 | 0.1 | 0.1 | 0.1 | 0.5 | 0.005 |
| Dimethyl polysiloxane (3) | 1.5 | 2.0 | 1.5 | — | 1.5 | 1.5 | 1.5 | 1.5 |
| Methylphenyl polysiloxane (4) | 1.5 | — | 1.5 | — | 1.5 | 1.5 | 1.5 | 1.5 |
| Methylphenyl polysiloxane (5) | — | — | — | 1.5 | — | — | — | — |
| Ethanol | 10 | 20 | 10 | 10 | 10 | 10 | 10 | 10 |
| Liquified petroleum gas | 10 | 10 | 10 | 10 | 10 | 10 | 10 | 10 |
| Water | 72.8 | 64.82 | 73.7 | 75.2 | 73.7 | 75.9 | 73.6 | 73.575 |

(1) Trade name: Gantrez ES-425 (product of GAF A.G.)
(2) Trade name: Silicon L-7001 (product of Nippon Uniker Co., Ltd.)
(3) Viscosity: 100 centistokes
(4) Viscosity: 300 centistokes
(4) Viscosity: 1,000 centistokes 1. An emulsion type hair cosmetic consisting essentially of:
(A) 0.1 to 5% by weight of a dimethylpolysiloxane polyoxyalkylene copolymer having a cloud point of 20° to 45° C. and represented by the following formula (I):

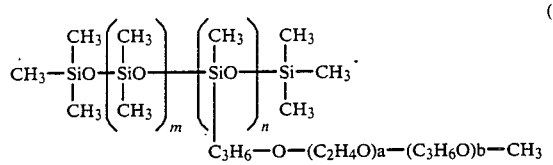

in which a represents a value of from 10 to 25, b represents a value of from 25 to 35, m represents a value of from 60 to 80 and n represents a value of from 3 to 8,
(B) 0.02 to 2.5% by weight of a non-ionic surface active agent having an HLB value of not less than 10,
(C) 0.01 to 0.5% by weight of an ionic surface active agent,
(D) 0.05 to 10% by weight of silicone oil,
(E) 0.1 to 10% by weight of a polymer for fixing hair, which is soluble in water or an ethanol/water mixture of 50/50 weight ratio,
(F) 2 to 40% by weight of ethanol, and
(G) 30 to 97% by weight of water.